United States Patent
Bishop et al.

(10) Patent No.: US 10,915,934 B2
(45) Date of Patent: Feb. 9, 2021

(54) METHODS FOR AUTOMATED PROCESSING OF HYBRID ELECTRONIC INVOICE DATA AND DEVICES THEREOF

(71) Applicant: Mitchell International, Inc., San Diego, CA (US)

(72) Inventors: Michael Bishop, Mill Valley, CA (US); James Freeman, Jacksonville, FL (US); Alma Martinez, Chino Hills, CA (US); David Torrence, San Diego, CA (US); Roger Kartchner, Riverton, UT (US); Rebecca Morgan, Kansas City, MO (US)

(73) Assignee: Mitchell International, Inc., San Diego, CA (US)

( * ) Notice: Subject to any disclaimer, the term of this patent is extended or adjusted under 35 U.S.C. 154(b) by 232 days.

(21) Appl. No.: 16/159,400

(22) Filed: Oct. 12, 2018

(65) Prior Publication Data
US 2019/0114682 A1    Apr. 18, 2019

Related U.S. Application Data

(60) Provisional application No. 62/571,923, filed on Oct. 13, 2017.

(51) Int. Cl.
*G06Q 30/04* (2012.01)
*G16H 40/20* (2018.01)
*G06F 40/117* (2020.01)
*G06F 40/205* (2020.01)

(52) U.S. Cl.
CPC ........... *G06Q 30/04* (2013.01); *G06F 40/117* (2020.01); *G06F 40/205* (2020.01); *G16H 40/20* (2018.01)

(58) Field of Classification Search
None
See application file for complete search history.

(56) References Cited

U.S. PATENT DOCUMENTS 8,666,772 B2 *   3/2014   Kaniadakis ........... G06F 19/328
                                                              705/2

OTHER PUBLICATIONS

Wikipedia, "Healthcare Common Procedure Coding System", Feb. 2, 2018, 2 pages, Retrieved from the Internet: <https://en.wikipedia.org/wiki/Healthcare_Common_Procedure_Coding_System>.

* cited by examiner

*Primary Examiner* — Paul Danneman
(74) *Attorney, Agent, or Firm* — Sheppard Mullin Richter & Hampton LLP (57) ABSTRACT

Methods, non-transitory computer readable media, and apparatuses for automated processing of hybrid electronic invoice data include identifying at least a first type of charge data from one or more other types of charge data in received hybrid electronic invoice data based on one or more parsing techniques. The first type of charge data is disassembled from the received hybrid electronic invoice data based on the identification. The disassembled first type of charge data is adjudicated based on execution of one of a plurality of sets of adjudication procedures identified to correspond to the disassembled first type of charge data. The received hybrid electronic invoice data is transformed with the adjudicated first type of charge data. The transformed electronic invoice data is provided for additional processing.

18 Claims, 4 Drawing Sheets

| Line | Date | POS Rev./Proc. Code | Charges | Dx. | Units | IRR | Description CBR PPO | ONR | NDG | Explanation Code(s) ADJ Allow. |
|---|---|---|---|---|---|---|---|---|---|---|
| 1 | | 99203 | 128.47 | A | 1 | | OFFICE/OUTPATIENT VISIT 12.85 | | | G4, 136 119.62 |
| 2 | | 73564 | 69.37 | A | 1 | 13.03 | X-RAY EXAM KNEE 4 OR MOR 3.65 | | | G1, 790, G4, 136 30.89 |
| 3 | | 73564 | 69.37 | A | 1 | 13.03 | X-RAY EXAM KNEE 4 OR MOR 5.65 | | | G1, 790, G4, 136 50.99 |
| 4 | | L1820 | 139.11 | A | 1 | | KO ELAS W/ CONDYLE PADS 13.81 | | | G4, 136 123.30 |
| 5 | | NDC#: 63746-0194-05 | 96.03 | A | 500A | 48.15 | NAPROXEN SODIUM TABS MG 4.99 | | | G1, 488, G4, 136 44.89 |
| 6 | | E0110-NU | 84.81 | A | 1 | | CRUTCH FOREARM PAIR 8.40 | | | G4, 136 75.61 |
| 7 | | A9900 | 16.50 | A | 1 | | MISCELLANEOUS DME SUPPLY 1.65 | | | G4, 136 14.85 |

400 → (table)
404 → (columns)
402 → (column)
404 → (columns)
406 → (Explanation Codes column)

FIG. 4

METHODS FOR AUTOMATED PROCESSING OF HYBRID ELECTRONIC INVOICE DATA AND DEVICES THEREOF

This application claims the benefit of U.S. Provisional Patent Application Ser. No. 62/571,923, filed Oct. 13, 2017, which is hereby incorporated by reference in its entirety.

FIELD

This technology generally relates to methods and devices for automated processing of a selected portion of hybrid electronic invoice data and, in particular, hybrid electronic invoice data with one or more pharmacy charges and non-pharmacy charges.

BACKGROUND

In a number of different industries, there is a growing trend to electronically manage and process invoice data. Processing invoice data in this manner provides a number of benefits including improved speed, accuracy, and consistency.

Unfortunately, this processing of electronic invoice data also has resulted in new technical issues and problems. For example, electronic invoice data within a particular industry may often be received in a number of different formats and may comprise many different types of charge data that needs to be processed in different manners under different standards. By way of example, in the medical industry physicians are often combining non-pharmacy charge data relating to, for example, diagnosis and treatment of a patient and related medical supplies or equipment, such as braces, with pharmacy charge data relating to, medication dispensed by the treating physician to the patient. These different types of charge data in electronic invoices in different formats must be identified and accurately processed in a timely manner under different sets of adjudication procedures and time frames. Unfortunately, there currently are no satisfactory technical solutions for accurately identifying, processing, and adjudicating different portions of hybrid electronic invoice data as needed or for transforming the electronic invoice data during this processing of the hybrid electronic invoice data. As a result, the speed, accuracy, consistency, and scalability of managing and processing electronic invoice data is lost when hybrid electronic invoice data is being processed and substantial processing errors have occurred with these hybrid electronic invoices.

SUMMARY

A method for automated processing of hybrid electronic invoice data includes identifying, by an invoice management computing apparatus, at least a first type of charge data from one or more other types of charge data in received hybrid electronic invoice data based on one or more parsing techniques. The first type of charge data is disassembled, by the invoice management computing apparatus, from the received hybrid electronic invoice data based on the identification. The disassembled first type of charge data is adjudicated, by the invoice management computing apparatus, based on execution of one of a plurality of sets of adjudication procedures identified to correspond to the disassembled first type of charge data. The received hybrid electronic invoice data is transformed, by the invoice management computing apparatus, with the adjudicated first type of charge data. The transformed electronic invoice data is provided, by the invoice management computing apparatus, for additional processing.

A non-transitory computer readable medium having stored thereon instructions for automated processing of hybrid electronic invoice data comprising executable code which when executed by a processor, causes the processor to identify at least a first type of charge data from one or more other types of charge data in received hybrid electronic invoice data based on one or more parsing techniques. The first type of charge data is disassembled from the received hybrid electronic invoice data based on the identification. The disassembled first type of charge data is adjudicated based on execution of one of a plurality of sets of adjudication procedures identified to correspond to the disassembled first type of charge data. The received hybrid electronic invoice data is transformed with the adjudicated first type of charge data. The transformed electronic invoice data is provided for additional processing.

A computing apparatus having a memory coupled to a processor which is configured to be capable of executing programmed instructions stored in the memory to identify at least a first type of charge data from one or more other types of charge data in received hybrid electronic invoice data based on one or more parsing techniques. The first type of charge data is disassembled from the received hybrid electronic invoice data based on the identification. The disassembled first type of charge data is adjudicated based on execution of one of a plurality of sets of adjudication procedures identified to correspond to the disassembled first type of charge data. The received hybrid electronic invoice data is transformed with the adjudicated first type of charge data. The transformed electronic invoice data is provided for additional processing.

This technology generally relates to methods, non-transitory computer readable media and apparatuses for more effective and efficient automated processing of hybrid electronic invoice data. With this technology, hybrid electronic invoice data in a variety of formats can be processed with the different types of charge data identified and adjudicated in accordance with the appropriate set of adjudication procedures. By way of example, this technology is able to more effectively process hybrid electronic invoice data with pharmacy charge data and non-pharmacy charge data. Additionally, this technology is able to uniquely utilize machine learning to more effectively and cost efficiently identifies types of charge data in the received hybrid electronic invoice data.

DETAILED DESCRIPTION

Figure 1:
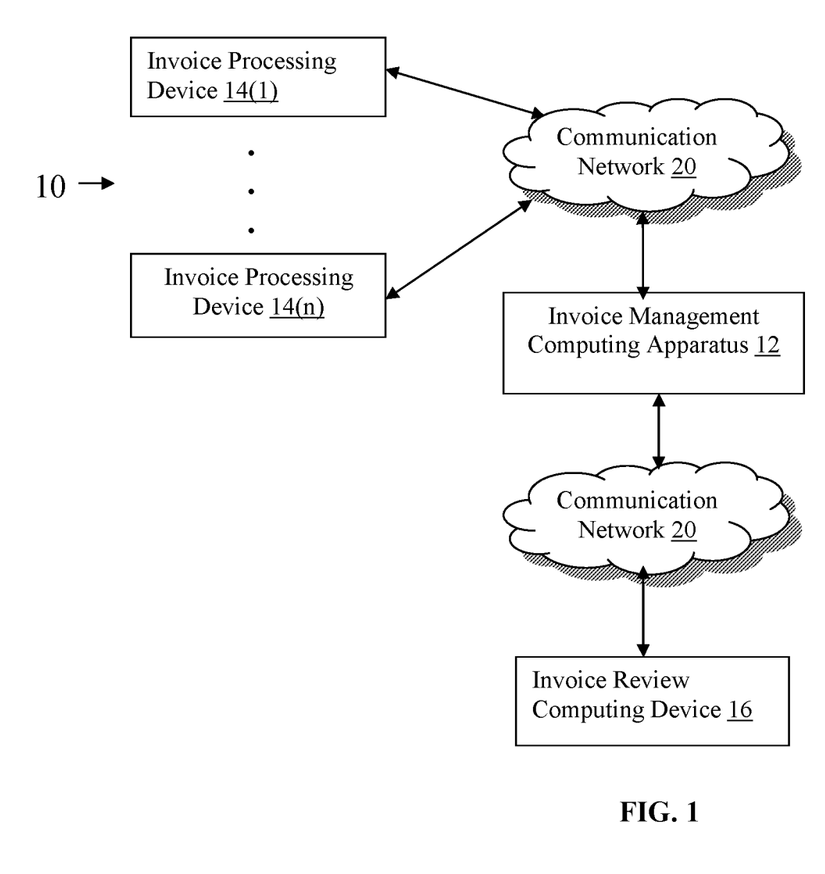
FIG. 1 is a block diagram of an environment with an example of an invoice management computing apparatus that optimizes automated processing of hybrid electronic invoice data.
Figure 2:
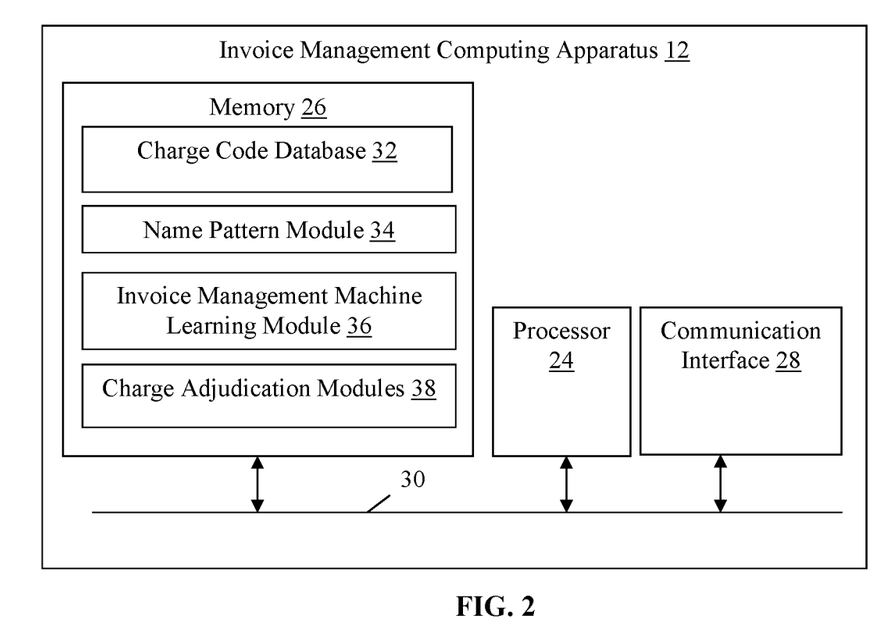
FIG. 2 is a block diagram of the example of the invoice management computing apparatus shown in FIG. 1.

An environment 10 with an example of an invoice management computing apparatus 12 that evaluates and processes a selected portion of an electronic invoice data is illustrated in FIGS. 1-2. In this particular example, the environment 10 includes the invoice management computing apparatus 12, invoice input devices 14(1)-14(n), an administrative computing device 16, an invoice review computing device 18 coupled via one or more communication networks 20, although the environment could include other types and numbers of systems, devices, components, and/or other elements as is generally known in the art and will not be illustrated or described herein. This technology provides a number of advantages including providing methods, non-transitory computer readable medium, and apparatuses for improving prior issues with automated processing of hybrid electronic invoice data, such as an electronic invoice data with pharmacy charge data and non-pharmacy charge data.

Referring more specifically to FIGS. 1-2, the invoice management computing apparatus 12 is programmed to optimize prior automated processing of hybrid electronic invoice data, such as an electronic invoice data with one or more pharmacy charge data and non-pharmacy charge data as illustrated and described herein, although the apparatus can perform other types and/or numbers of functions or other operations and this technology can be utilized with other types of claims. In this particular example, the invoice management computing apparatus 12 includes a processor 24, a memory 26, and a communication interface 28 which are coupled together by a bus 30, although the invoice management computing apparatus 12 may include other types and/or numbers of physical and/or virtual systems, devices, components, and/or other elements in other configurations.

The processor 24 in the invoice management computing apparatus 12 may execute one or more programmed instructions stored in the memory 26 for improving automated processing of hybrid electronic invoice data as illustrated and described in the examples herein, although other types and numbers of functions and/or other operation can be performed. The processor 24 in the invoice management computing apparatus 12 may include one or more central processing units and/or general purpose processors with one or more processing cores, for example.

The memory 26 in the invoice management computing apparatus 12 stores the programmed instructions and other data for one or more aspects of the present technology as described and illustrated herein, although some or all of the programmed instructions could be stored and executed elsewhere. A variety of different types of memory storage devices, such as a random access memory (RAM) or a read only memory (ROM) in the system or a floppy disk, hard disk, CD ROM, DVD ROM, or other computer readable medium which is read from and written to by a magnetic, optical, or other reading and writing system that is coupled to the processor 24, can be used for the memory 26. In this particular example, the memory 26 includes a pharmacy code data base 32, a name pattern module 34, an invoice management machine learning module 36, and charge adjudication modules 38, although the memory 26 can comprise other types and/or numbers of other modules, programmed instructions and/or data and these stored instructions, data, and/or modules may be on and executed by other systems, devices, components, and/or other elements.

In this particular example, the charge code database 32 is stored and used by the invoice management computing apparatus 12 to assist with the identification of different types of charge data within an electronic invoice, although other types and/or numbers of other code databases may be stored and used. Additionally, in this example the one or more types of stored charge codes stored in the charge code database 32 may comprise one or more of Healthcare Common Procedure Coding System (HCPCS) codes, Current Procedural Terminology (CPT) codes, International Classification of Diseases (ICD) codes, and/or National Drug Codes (NDC), although other types and/or numbers of other codes may be used.

Additionally, the name pattern module 34 may be executed by the invoice management computing apparatus 12 to identify different types of charge data in the received hybrid electronic invoice data by comparing name data in the received hybrid electronic invoice data with stored named data.

Further, the invoice management machine learning module 36 may comprise artificial intelligence that is utilized by the invoice management computing apparatus 12 to identify different types of charge data within hybrid electronic invoice data. In this particular example, the invoice management machine learning module 36 may comprise a deep neural network (DNN) that may be executed and used to identify different types of charge data in the hybrid electronic invoice data, although other types of artificial intelligence may be used. The DNN may have a structure and synaptic weights trained using semi-supervised machine learning techniques in conjunction with labelled and unlabeled types of charge data to encode knowledge for identifying different types of charge data. This DNN executed by the invoice management computing apparatus 12 in this example provides significantly faster and more cost efficient identification of different types of charge data in the electronic invoice data. By way of another example, the invoice management machine learning module 36 may further comprise artificial intelligence that is utilized by the invoice management computing apparatus 12 to recognize and detect any lines of data in the hybrid electronic invoice data that are incorrectly coded, such as an incorrect NDC code for the drug, an incorrect billing form used to generate the hybrid electronic invoice data, or an incorrect procedure code, whether unintentional or intentional, to identify errors as well as any fraud.

The charge adjudication module 38 may comprise programmed instructions relating to different sets of stored adjudication procedures and/or rules to automatically adjudicate different types of charge data, such as pharmacy data and non-pharmacy data by way of example only. By way of example, automated adjudication may involve identifying and applying one of a plurality of stored procedures and/or rules correlated to the identified type of charge data to determine adjudication data, such as about compensability, price and/or clinical suitability of the identified type of charge data, although other types of automated adjudication may be utilized. For pharmacy data this may, for example, entail determining adjudication data on: Compensability—is the drug in pharmacy data addressing an injury or condition covered by the claim in the hybrid electronic invoice data; Price—Is the price for the drug in the pharmacy data corresponding to state fee schedules and/or regulations and/or recorded contractual agreements; and/or Clinical suitability—are there any issues with the drug in the pharmacy data, such as with drug interactions for the client identified in the hybrid electronic invoice data or is there a suitable generic equivalent drug by way of example. Additionally, the determine adjudication data may further comprise other types of information, such as added commentary data. Accordingly, the charge adjudication module 38 may adjudicate part or all of the different identified types of charge data into new adjudicated data that is used to transform the hybrid electronic invoice data.

The communication interface 28 in the invoice management computing apparatus 12 operatively couples and communicates between one or more of the invoice input devices 14(1)-14(n) and the invoice review computing device 16, which are all coupled together by one or more of the communication networks 20, although other types and numbers of communication networks or systems with other types and numbers of connections and configurations to other devices and elements may be used. By way of example only, the communication networks 20 can use TCP/IP over Ethernet and industry-standard protocols, including NFS, CIFS, SOAP, XML, LDAP, SCSI, and SNMP, although other types and numbers of communication networks, can be used. The communication networks 20 in this example may employ any suitable interface mechanisms and network communication technologies, including, for example, any local area network, any wide area network (e.g., Internet), teletraffic in any suitable form (e.g., voice, modem, and the like), Public Switched Telephone Network (PSTNs), Ethernet-based Packet Data Networks (PDNs), and any combinations thereof and the like.

In this particular example, each of the invoice input devices 14(1)-14(n) may input and provide hybrid electronic invoice data, such as hybrid electronic medical invoice data with pharmacy charge data and non-pharmacy charge data to be evaluated and processed by the invoice management computing apparatus 12, although the hybrid electronic medical invoice data can be obtained from other sources, including by converting paper invoices into hybrid electronic medical invoice data as is generally known in the art.

The invoice review computing device 16 may further process the other charge data in the hybrid electronic invoice data or all of the hybrid electronic invoice data after the selected portion of charge data has been identified, disassembled, and adjudicated, although other types and/or numbers of systems, devices, components, and/or other elements may be used and the invoice review computing device 16 could be processing the hybrid electronic invoice data in other manners. In this particular example, the invoice review computing device 16 may comprise various combinations and types of storage hardware and/or software and represent a system with multiple network server devices in a data storage pool, which may include internal or external networks. Various network processing applications, such as CIFS applications, NFS applications, HTTP Web Network server device applications, and/or FTP applications, may be operating on invoice review computing device 16.

Each of the invoice input devices 14(1)-14(n) and the invoice review computing device 16 may include a processor, a memory, and a communication interface, which are coupled together by a bus or other link, although other type and/or numbers of other devices and/or nodes as well as other network elements could be used.

Although the exemplary network environment 10 with the invoice management computing apparatus 12, the invoice input devices 14(1)-14(n), the invoice review computing device 16, and the communication networks 20 are described and illustrated herein, other types and numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

In addition, two or more computing systems or devices can be substituted for any one of the systems or devices in any example. Accordingly, principles and advantages of distributed processing, such as redundancy and replication also can be implemented, as desired, to increase the robustness and performance of the devices, apparatuses, and systems of the examples. The examples may also be implemented on computer system(s) that extend across any suitable network using any suitable interface mechanisms and traffic technologies, including by way of example only teletraffic in any suitable form (e.g., voice and modem), wireless traffic media, wireless traffic networks, cellular traffic networks, G3 traffic networks, Public Switched Telephone Network (PSTNs), Packet Data Networks (PDNs), the Internet, intranets, and combinations thereof.

The examples also may be embodied as a non-transitory computer readable medium having instructions stored thereon for one or more aspects of the present technology as described and illustrated by way of the examples herein, as described herein, which when executed by the processor, cause the processor to carry out the steps necessary to implement the methods of this technology as described and illustrated with the examples herein.

Figure 3:
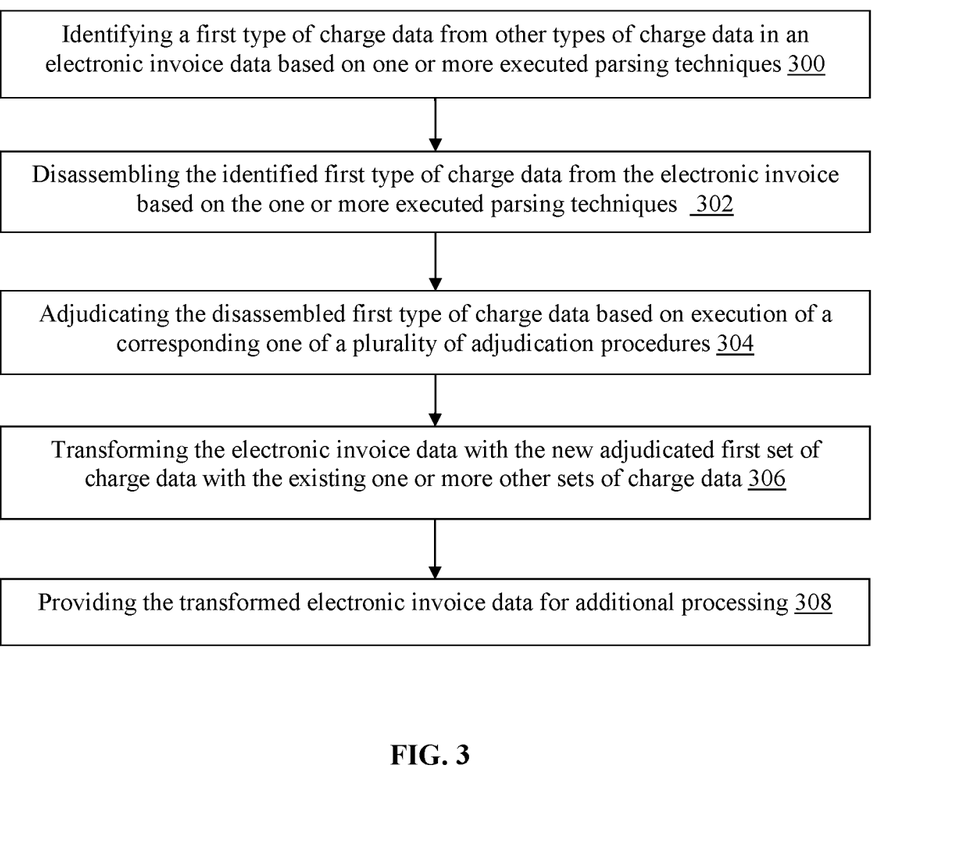
FIG. 3 is a flow chart of an example of a method for automated processing of hybrid electronic invoice data.

An example of a method for automated processing of hybrid electronic invoice data will now be illustrated and described with reference to FIGS. 1-3. In step 300, at least a first type of charge data is identified by the invoice management computing apparatus 12 from one or more other types of charge data in hybrid electronic invoice data based on one or more parsing techniques. The hybrid electronic invoice data may be input and received from one or more of the invoice input devices 14(1)-14(n), although the hybrid electronic invoice data may be obtained from other sources in other manners. In this particular example, the invoice management computing apparatus 12 identifies pharmacy charge data 402 in line 5 and non-pharmacy charge data 404 in lines 1-4 and 6-7 in hybrid electronic invoice data 400 as shown in the example in FIG. 4, although other types and/or portions of charge data in the hybrid electronic invoice data 400 may be identified.

Figure 4:
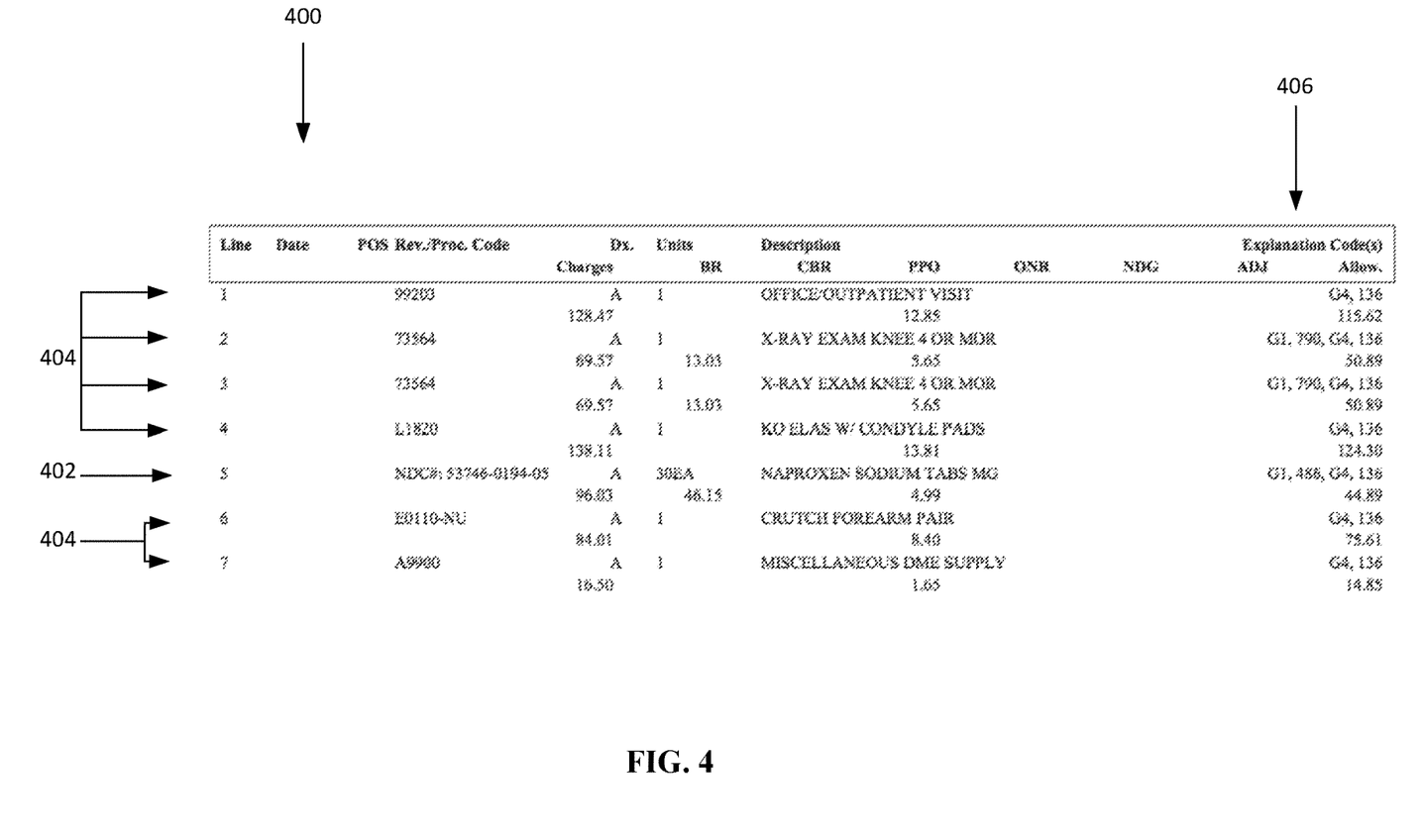
FIG. 4 is a diagram of an example of one of a plurality of different formats of hybrid electronic invoice data with pharmacy charge data and non-pharmacy charge data.

Additionally, in this particular example one or more parsing techniques may be used by the invoice management computing apparatus 12 to identify different types of charge data in the hybrid electronic invoice. By way of example, the invoice management computing apparatus 12 may identify different types of charge data in the hybrid electronic invoice based on a determined correspondence above a stored set threshold of portions of the hybrid electronic invoice data and one or more types of stored charge codes, although other types and/or numbers of techniques, alone or on combination, may be used to identify different types of charge data. An example of charge codes 406 in hybrid electronic invoice data 400 is illustrated in FIG. 4. The codes may be stored in the charge code database 32 and may comprise one or more of Healthcare Common Procedure Coding System (HCPCS) codes, Current Procedural Terminology (CPT) codes, International Classification of Diseases (ICD) codes, or National Drug Codes (NDC), although other types and/or numbers of other codes may be used. Further, by way of example, the invoice management computing apparatus 12 based on execution of trained artificial intelligence, such as invoice management machine learning module 36 comprising, for example, a deep neural network (DNN), can be used to identify and differentiate between different types of charge data within hybrid electronic invoice data, although each of these and/or other techniques, alone or in combination, may be used to identify different types of charge data.

In step 302, once a first type of charge data is identified from one or more other types of charge data in the hybrid electronic invoice, which in this example may be pharmacy charge data 402, then this first charge data may be disassembled by the invoice management computing apparatus 12 from the other type or types of charge data, such as non-pharmacy charge data 404, in the hybrid electronic invoice data 400 in this example. The disassembling of the identified first type of charge data from the other type or types of charge data in the hybrid electronic invoice data may include tagging by the invoice management computing apparatus 12 each identified location in the hybrid electronic invoice data with the identified first type of charge data. Once each location in the hybrid electronic invoice data is tagged, the identified first type of charge data may be extracted from the other type or types of charge data in the hybrid electronic invoice data by the invoice management computing apparatus 12. Next, the remaining type or types of charge data and tags in the disassembled hybrid electronic invoice data may be stored by the invoice management computing apparatus 12.

In step 304, the invoice management computing apparatus 12 may implement an automated adjudication of the disassembled first type of charge data based on execution of a corresponding one of a plurality of the charge adjudication modules 38 corresponding with the identified type of charge data. By way of example, the disassembled first type of charge data may comprise pharmacy data 402 which is adjudicated based on automated application of one more pharmacy adjudication procedures, rules, and/or other standards obtained from a corresponding one of a plurality of the charge adjudication modules 38 related to pharmacy data. Additionally, as part of the adjudication, the invoice management computing apparatus 12 may obtain associated adjudication commentary data which is combined with the adjudicated first type of charge data, although other types and/or amounts of other information may also be obtained.

By way of an more detailed example, this automated adjudication may involve identifying and applying by the invoice management computing apparatus 12 one of a plurality of stored adjudication procedures, rules, and/or other standards correlated to the identified type of charge data to determine adjudication data, such as about compensability, price and/or clinical suitability of the identified type of charge data, although other types of automated adjudication may be utilized. For pharmacy data this may, for example, entail determining adjudication data on: Compensability—is the drug identified in pharmacy data addressing an injury or condition covered by the claim in the hybrid electronic invoice data; Price—Is the price for the drug in the pharmacy data corresponding to state fee schedules and/or regulations and/or recorded contractual agreements; and/or Clinical suitability—are there any issues with the drug identified in pharmacy data, such as with a drug interaction with stored data on another prescribed drug for the client identified in the hybrid electronic invoice data or in another example is there a suitable generic equivalent drug for the drug identified in pharmacy data. A variety of different types of automated adjudication may be applied by the invoice management computing apparatus 12 on the pharmacy data resulting in transformed adjudicated pharmacy data.

In step 306, the invoice management computing apparatus 12 may transform the disassembled hybrid electronic invoice data with the remaining type or types of charge data and tags with the new adjudicated first type of charge data that is partially or completely replacing the prior first type of charge data based on the adjudication. In this example, the invoice management computing apparatus may correlate the identified stored tagging for each location of each portion of the identified first type of charge data in the disassembled hybrid electronic invoice data with the adjudicated first type of charge data. Next, the invoice management computing apparatus may implement a transformation at each tagged location in the disassembled hybrid electronic invoice data based on the correlation, the corresponding portion of the identified first type of charge data, and the adjudicated first type of charge data. By way of example, the invoice management computing apparatus may determine to transform the hybrid electronic invoice by inserting part or all of the adjudicated first type of charge data with part or all of the prior first type of charge data at corresponding portions of the prior location of the related first type of charge data along with any inserted adjudication commentary data, although other types of transformation may be implemented.

In step 308, the transformed electronic invoice data may be provided by the invoice management computing apparatus 12 to the invoice review computing device 18 for additional processing on the one or more other sets of charge data in the reassembled electronic invoice data or the entire reassembled electronic invoice data. Alternatively, the invoice management computing apparatus 12 may execute an automated adjudication of the other type or types of charge data and further transform the hybrid electronic invoice data as described earlier with reference to the first type of charge data by way of a further example.

Accordingly, as illustrated by way of the examples herein the claimed technology provides methods, non-transitory computer readable medium, and apparatuses for improving prior issues with automated processing of a portion of hybrid electronic invoice data, such as hybrid electronic invoice data with one or more pharmacy charge data and non-pharmacy charge data. By way of example, this technology addresses the problem of identifying and accurately adjudicating pharmacy charge data when that pharmacy charge data is interspersed with non-pharmacy charge data in an invoice after a corresponding pharmacy product, such as a prescription drug, has already been dispensed. Accordingly, the claimed technology enables insurance providers an automated technique to accurately and effectively apply cost and clinical controls to different types of charge data, such as pharmacy data, that is currently outside their reach.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for automated processing of hybrid electronic invoice data, the method comprising:
   identifying, by an invoice management computing apparatus, a pharmacy charge data record and a type of charge data associated with the pharmacy charge data record from a plurality of pharmacy charge data records and non-pharmacy charge data records in a received hybrid electronic invoice, by using a machine learning algorithm trained on historic hybrid invoice data comprising a plurality of pharmacy records, each pharmacy record characterized by a type of charge data from a plurality of types;

extracting, by the invoice management computing apparatus, the charge data associated with the identified pharmacy charge data record from the received hybrid electronic invoice by tagging one or more locations in the received hybrid electronic invoice associated with the identified pharmacy charge data record of the identified charge data type;

determining at least one set of adjudication rules for adjudicating the identified pharmacy charge data record based on the identified type of charge data;

determining at least one adjudication commentary for the identified charge data associated with the identified pharmacy charge data type based on the determined set of adjudication rules;

adjudicating, by the invoice management computing apparatus, the extracted charge data associated with the identified pharmacy charge data record charge data by applying the at least one set of determined adjudication rules to determine adjudication data comprising at least one of compensability data, price data, and clinical suitability data;

transforming, by the invoice management computing apparatus, the received hybrid electronic invoice data by replacing the identified type of charge data with the determined compensability data, price data, and clinical suitability data; and providing, by the invoice management computing apparatus, the transformed electronic invoice data for additional processing;

wherein the type of charge data associated with the pharmacy charge data record may be specified by one or more stored charge codes.

2. The method of claim 1, wherein identifying a pharmacy charge data record and the type of charge data associated with the pharmacy charge data record comprises using a one or more parsing techniques comprising a determination of a correspondence between any portions of the hybrid electronic invoice data and one or more types of stored charge codes, stored naming pattern data, or stored results from execution of at least one adaptive learning technique.

3. The method of claim 2, wherein the one or more stored charge codes comprise one or more of Healthcare Common Procedure Coding System (HCPCS) codes, Current Procedural Terminology (CPT) codes, International Classification of Diseases (ICD) codes, or National Drug Codes (NDC).

4. The method of claim 1, further comprises
storing each of the one or more tagged locations associated with the identified pharmacy charge data record of the identified charge data type.

5. The method of claim 4, wherein the transforming the received hybrid electronic invoice data with the adjudicated data comprises:
correlating, by the invoice management computing apparatus, the identified tagging for each location of each portion of the identified type of charge data in the received hybrid electronic invoice with the adjudication data;
determining, by the invoice management computing apparatus, the transformation for each location based on the correlation, the corresponding portion of the identified data type of charge data, and the adjudication data; and
reassembling, by the invoice management computing apparatus, the adjudication data in the received hybrid electronic invoice based on the determined transformation for each location.

6. The method of claim 1, wherein the adjudicating the identified type of charge data comprises:
inserting, by the invoice management computing apparatus, the determined adjudication commentary data in with the adjudicated type of charge data.

7. A non-transitory computer readable medium having stored thereon instructions for automated processing of hybrid electronic invoice data comprising executable code which when executed by a processor, causes the processor to:
identify pharmacy charge data record and a type of charge data associated with the pharmacy charge data record from a plurality of pharmacy charge data records and non-pharmacy charge data records in a received hybrid electronic invoice, by using a machine learning algorithm trained on historic hybrid invoice data comprising a plurality of pharmacy records, each pharmacy record characterized by a type of charge data from a plurality of types;
extract the charge data associated with the identified pharmacy charge data record from the received hybrid electronic invoice by tagging one or more locations in the received hybrid electronic invoice associated with the identified pharmacy charge data record of the identified charge data type;
determining at least one set of adjudication rules for adjudicating the identified pharmacy charge data record based on the identified type of charge data;
determine at least one adjudication commentary data for the identified charge data associated with the identified pharmacy charge data type based on the determined set of adjudication rules;
adjudicate the extracted charge data associated with the identified pharmacy charge data record charge data by applying the at least one set of determined plurality of sets of adjudication rules to determine adjudication data comprising at least one of compensability data, price data, and clinical suitability data;
transform the received hybrid electronic invoice data by replacing the identified type of charge data with the determined compensability data, price data, and clinical suitability data; and
provide the transformed electronic invoice data for additional processing;
wherein the type of charge data associated with the pharmacy charge data record may be specified by one or more stored charge codes.

8. The medium of claim 7, wherein identifying a pharmacy charge data record and the type of charge data associated with the pharmacy charge data record comprises using a one or more parsing techniques comprise a determination of a correspondence between any portions of the received hybrid electronic invoice data and one or more types of stored charge codes, stored naming pattern data, or stored results from execution of at least one adaptive learning technique.

9. The medium of claim 8, wherein the one or more stored charge codes comprise one or more of Healthcare Common Procedure Coding System (HCPCS) codes, Current Procedural Terminology (CPT) codes, International Classification of Diseases (ICD) codes, or National Drug Codes (NDC).

10. The medium of claim 7, wherein the executable code which when executed by a processor, further causes the processor to:
store each of the one or more tagged locations associated with the identified pharmacy charge data record of the identified charge data type.

11. The medium of claim 10, wherein the executable code which when executed by a processor, further causes the processor to:
correlate the identified tagging for each location of each portion of the identified type of charge data in the received hybrid electronic invoice with the adjudication data;
determine the transformation for each location based on the correlation, the corresponding portion of the identified type of charge data, and the adjudication data; and
reassemble the adjudicated first type of charge data in the adjudication data in the received hybrid electronic invoice based on the determined transformation for each location.

12. The medium of claim 7, wherein the adjudicate the identified type of charge data further comprises executable code which when executed by a processor, causes the processor to:
insert the determined adjudication commentary data in with the adjudicated type of charge data.

13. A computing apparatus comprising:
a processor; and a memory coupled to the processor which is configured to be capable of executing programmed instructions stored in the memory to:
identify a pharmacy charge data record and a type of charge data associated with the pharmacy charge data from a plurality of pharmacy charge data records and non-pharmacy charge data records in a received hybrid electronic invoice data, by using a machine learning algorithm trained on historic hybrid invoice data comprising a plurality of pharmacy records, each pharmacy record characterized by a type of charge data from a plurality of types;
extract the charge data associated with the identified pharmacy charge data record from the received hybrid electronic invoice by tagging one or more locations in the received hybrid electronic invoice associated with the identified pharmacy charge data record of the identified charge data type;
determining at least one set of adjudication rules for adjudicating the identified pharmacy charge data record based on the identified type of charge data;
determine at least one adjudication commentary data for the identified charge data associated with the identified pharmacy charge data type based on the determined set of adjudication rules;
adjudicate the extracted charge data associated with the identified pharmacy charge data record charge data by applying the at least one set of determined adjudication rules to determine adjudication data comprising at least one of compensability data, price data, and clinical suitability data;
transform the received hybrid electronic invoice data by replacing the identified type of charge data with the determined compensability data, price data, and clinical suitability data; and
provide the transformed electronic invoice data for additional processing;
wherein the type of charge data associated with the pharmacy charge data record may be specified by one or more stored charge codes.

14. The apparatus of claim 13, wherein identifying a pharmacy charge data record and the type of charge data associated with the pharmacy charge data record comprises using one or more parsing techniques comprising a determination of a correspondence between any portions of the received hybrid electronic invoice data and one or more types of stored charge codes, stored naming pattern data, or stored results from execution of at least one adaptive learning technique.

15. The apparatus of claim 14, wherein the one or more stored charge codes comprise one or more of Healthcare Common Procedure Coding System (HCPCS) codes, Current Procedural Terminology (CPT) codes, International Classification of Diseases (ICD) codes, or National Drug Codes (NDC).

16. The apparatus of claim 13, wherein identification, the processor coupled to the memory is further configured to be capable of executing at least one additional programmed instruction stored in the memory to:
store each of the one or more tagged locations associated with the identified pharmacy charge data record of the identified charge data type.

17. The apparatus of claim 16, wherein
the processor coupled to the memory is further configured to be capable of executing at least one additional programmed instruction stored in the memory to:
correlate the identified tagging for each location of each portion of the identified type of charge data in the received hybrid electronic invoice with the adjudication data;
determine the transformation for each location based on the correlation, the corresponding portion of the identified data type of charge data, and the adjudication data; and
reassemble the adjudication data in the received hybrid electronic invoice data based on the determined transformation for each location.

18. The apparatus of claim 13, wherein the processor coupled to the memory is further configured to be capable of executing at least one additional programmed instruction stored in the memory to
insert the determined adjudication commentary data in with the adjudicated first type of charge data.

* * * * *

UNITED STATES PATENT AND TRADEMARK OFFICE
CERTIFICATE OF CORRECTION

| | |
|---|---|
| PATENT NO. | : 10,915,934 B2 |
| APPLICATION NO. | : 16/159400 |
| DATED | : February 9, 2021 |
| INVENTOR(S) | : Michael Bishop et al. |

It is certified that error appears in the above-identified patent and that said Letters Patent is hereby corrected as shown below:

In the Claims

Column 12, Claim 17, Line 49 that reads "electronic invoice data based on the determined transformation" should read -- electronic invoice based on the determined transformation --

Column 12, Claim 18, Line 56 that reads "with the adjudicated first type of charge data." should read -- with the adjudicated type of charge data. --

Signed and Sealed this
Twenty-ninth Day of August, 2023

Katherine Kelly Vidal
*Director of the United States Patent and Trademark Office*